(12) United States Patent  (10) Patent No.: US 7,182,733 B2
Sauerland  (45) Date of Patent: Feb. 27, 2007

(54) CORDLESS STETHOSCOPE FOR HAZARDOUS MATERIAL ENVIRONMENTS

(76) Inventor: Keith A. Sauerland, 236 Cross Creek La., Lindenhurst, IL (US) 60046

( * ) Notice: Subject to any disclaimer, the term of this patent is extended or adjusted under 35 U.S.C. 154(b) by 245 days.

(21) Appl. No.: 10/644,111

(22) Filed: Aug. 20, 2003

(65) Prior Publication Data

US 2005/0043642 A1  Feb. 24, 2005

(51) Int. Cl.
*A61B 5/0245* (2006.01)
(52) U.S. Cl. .................. 600/528; 181/131; 381/67
(58) Field of Classification Search ............. 600/528, 600/586; 181/131, 136; 381/67
See application file for complete search history.

(56) References Cited

U.S. PATENT DOCUMENTS

| 6,186,957 B1* | 2/2001 | Milam ............... 600/528 |
| 6,340,350 B1 | 1/2002 | Simms |
| 6,533,736 B1* | 3/2003 | Moore ............... 600/586 |
| 6,544,198 B2 | 4/2003 | Chong et al. |
| 6,836,680 B2* | 12/2004 | Kuo ............... 600/513 |
| 6,852,084 B1* | 2/2005 | Boesen ............... 600/528 |
| 2004/0037429 A1* | 2/2004 | Candioty ............ 381/67 |
| 2005/0074130 A1* | 4/2005 | Brummel et al. ...... 381/67 |

* cited by examiner

*Primary Examiner*—George R. Evanisko
*Assistant Examiner*—Michael Kahelin
(74) *Attorney, Agent, or Firm*—Christopher J. Scott

(57) ABSTRACT

A cordless stethoscope for use in hazardous material environments comprising a fluid tight hand held sound sensing device having a stethoscope head for sensing auscultatory sounds, a transmitter for transmitting sounds sensed by the device, a receiver for receiving transmissions from the transmitter and an ear piece for converting the received transmissions into audible sound. The housing is sized and shaped for being grasped by a gloved hand and is fluid tight for decontamination purposes. The sound sensing device may further comprise a microphone for sensing otherwise inaudible voice communications from a patient. The transmitter and receiver preferably uses magnetic induction transmissions to transmit sounds through barriers such as hazardous material suits that may be worn by clinicians during treatment of patients in possible hazardous material situations.

8 Claims, 8 Drawing Sheets

CORDLESS STETHOSCOPE FOR HAZARDOUS MATERIAL ENVIRONMENTS

BACKGROUND OF THE INVENTION

1. Field of the Invention

The claimed invention generally relates to stethoscopes. More specifically, the claimed invention relates to cordless or wireless stethoscopes.

2. Description of the Prior Art

The threat of rapidly spreading infectious diseases to many different places around the world with little or no notice has significantly increased as international air travel has become commonplace. This threat coupled with increased concerns about possible biological and chemical attacks have resulted in a general increase in the awareness and preparedness of medical personnel to combat these types of threats. Doctors, nurses and emergency medical technicians typically use hazardous material protection suits, commonly known as HAZMAT suits, to protect themselves against these threats. HAZMAT suits completely isolate the healthcare workers from the surrounding environment forming a protective barrier against biological and chemical agents that may be presented by patients being cared for by the healthcare workers.

It has come to my attention during preparedness training for dealing with these threats that it is impossible for medical personnel to use a standard stethoscope when wearing a HAZMAT suit without compromising the integrity of the suit. Breaking the protective barrier of the HAZMAT suit defeats the purpose of wearing the suit and places medical personnel at risk. There are devices in the prior art that convey auscultatory information gathered by a stethoscope head in ways other than a standard stethoscope, but it has come to my attention that the prior art does not provide a stethoscope device compatible with hazardous material environments.

U.S. Pat. No. 6,340,350 issued to Simms discloses an electronic stethoscope and holder comprising a chest piece, an earpiece, and a casing for holding the chest piece and earpiece. The chest piece has a radio wave transmitter for transmitting auscultatory sounds from the chest piece to a receiver in the earpiece. This device could be used to transmit auscultatory sounds from the chest piece through a HAZMAT suit to a receiver within an earpiece worn by the suit wearer. However, this device does not address important concerns that are particular to hazardous material environments such as providing a device that is water tight so that it may be easily decontaminated after use in a hazardous material environment or providing a stethoscope head that is easily used while wearing gloves commonly employed by HAZMAT suits.

U.S. Pat. No. 6,544,198 issued to Chong et al. discloses a stethoscope system for self-examination whereby the condition of health of a particular individual can be diagnosed by comparing characteristic sound waves classified by diseases with sound waves generated from various parts of the individual's body. This device could also be used to transmit auscultatory sounds through a HAZMAT suit. However, this system does not provide a self contained and portable stethoscope device that can be used without other support structures in place and does not address the previously mentioned shortcomings that are particular in a hazardous material environment.

Therefore, there is a need for a stethoscope device designed for use by medical personnel wearing HAZMAT suits in hazardous material environments.

SUMMARY OF THE INVENTION

To accomplish the goal of providing a stethoscope device for use in hazardous material environments by personnel wear HAZMAT suits, the claimed invention provides a Cordless Stethoscope for Hazardous Material Environments.

An objective of the claimed invention is to provide a Cordless Stethoscope for Hazardous Material Environments that can cordlessly transmit information from a stethoscope head to a receiver within a hazardous material protection suit.

Another objective of the claimed invention is to provide a Cordless Stethoscope for Hazardous Material Environments having a fluid tight housing holding the stethoscope head and transmitter to allow easy decontamination of the stethoscope head.

A further objective of the claimed invention is to provide a Cordless Stethoscope for Hazardous Material Environments having a housing holding the stethoscope head that is designed to be held by a gloved hand.

An even further objective of the claimed invention is to provide a Cordless Stethoscope for Hazardous Material Environments having a microphone for picking up verbal communications that may not otherwise be audible through a hazardous material protection suit.

To achieve these objectives, as well as others that become apparent after reading this specification and viewing the appended drawings, the claimed invention provides a Cordless Stethoscope for Hazardous Material Environments.

The cordless stethoscope generally comprises a sound sensing device having a stethoscope head and a microphone for sensing and transmitting sounds from a patient, a receiver for receiving the transmissions, and earpieces for converting the received transmissions into audible sound for assessment by the person using the cordless stethoscope.

The sound sensing device comprises a fluid tight housing, a power source, a stethoscope head, a momentary activation switch, a microphone, a microphone activation switch and a transmitter. The sound sensing device is designed to be completely fluid tight so that the device may be decontaminated after use in a hazardous material environment without damaging the inner components of the device. The overall size and shape of the housing allows a user wearing gloves to compensate for the loss of fine motor skills.

The receiver generally comprises a receiver housing, a receiver, a receiver power source, an earpiece jack and a receiver volume control. Several different types of transmitters and receivers may be used in the cordless stethoscope, with magnetic induction transmission and reception being the preferred transmission means.

The cordless stethoscope for hazardous material is used by placing the earpieces within the ears of the user and the receiver within a pocket or cliped onto a belt within the HAZMAT suit worn by the user. The sound sensing device is used by placing the activated device adjacent a patient's body to gather auscultatory information that is transmitted via the transmitter to the receiver where the signal is converted into audible sound by the earpiece for assessment by the user of the cordless stethoscope.

BRIEF DESCRIPTION OF THE DRAWINGS

FIG. 1 shows a perspective view of the sound sensing device.

FIG. 2 shows another perspective view of the sound sensing device.

FIG. 3 shows a cross sectional view of the sound sensing device.

FIG. 4 shows how the sound sensing device is grasped and used.

FIG. 5 shows a cross sectional view of the sound sensing device having an optional microphone.

FIG. 6 shows a perspective view of the receiver.

FIG. 7 shows a cross sectional view of the receiver.

FIG. 8 shows a perspective view of the cordless stethoscope packaged as a kit.

DETAILED DESCRIPTION OF THE PREFERRED EMBODIMENT

Figure 8:
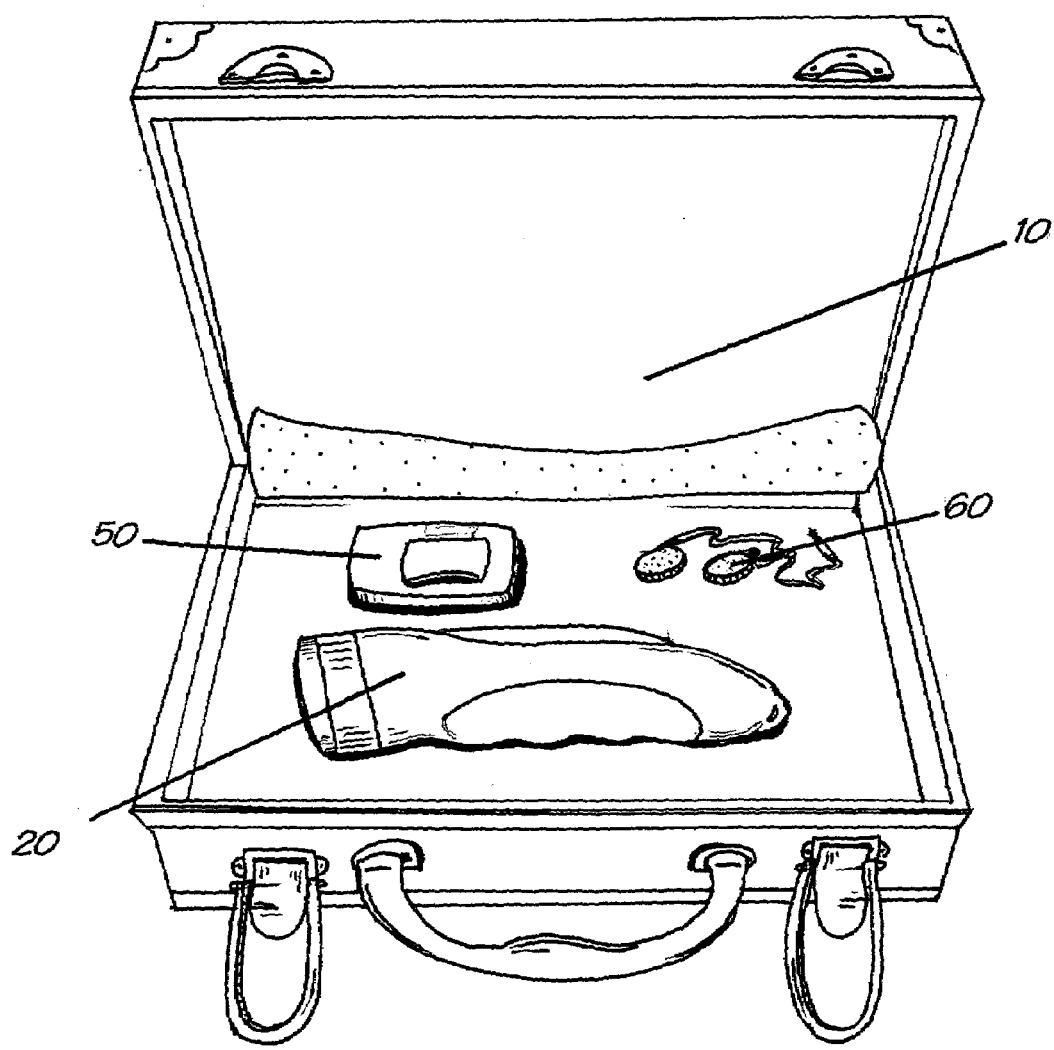
FIG. 8.

Turning now to the drawing figures, FIG. 8 shows the cordless stethoscope for use in hazardous material environments 10. The cordless stethoscope 10 generally comprises a sound sensing device 20 shown in FIGS. 1–4 having a stethoscope head 30 and a microphone 40 for sensing and transmitting sounds from a patient, a receiver 50 for receiving the transmissions, and earpieces 60 for converting the received transmissions into audible sound for the person using the cordless stethoscope 10.

The sound sensing device 20 shown in FIGS. 1–4 generally comprises a fluid tight housing 70, a power source 80, a stethoscope head 30, a momentary activation switch 100, a microphone 40, a microphone activation switch 110 and a transmitter 120. The sound sensing device 20 is designed to be completely fluid tight so that the device 20 may be decontaminated after use in a hazardous material environment without damaging the inner components of the device 20.

Heavy gloves are a necessary part of a HAZMAT suit to protect against biological and chemical agents. However, gloves that are commonly used with HAZMAT suits impede the use of fine motor skills involved in handling standard stethoscopes. To alleviate this problem, the fluid tight housing 70 shown in FIGS. 1–4 has been designed for users wearing gloves 130. The overall size and shape of the housing 70 allows a user wearing gloves 130 to compensate for the loss of fine motor skills. FIG. 3 shows how the sound sensing device 20 is typically held during use. The housing 70 also has a no slip grip 140 to provide an improved gripping surface for users wearing heavy gloves and a hand strap ring 150 or certain ring providing means for attaching the sound sensing device 20 about the hand of the user to prevent possible drop damage to the device 20. In other words, it is contemplated that the cordless stethoscope may comprise certain device-coupling means (such as hand strap ring 150) for removably coupling the cordless stethoscope or sound relaying device to another object.

The housing 70 has a head opening 160 for receiving the stethoscope head 30, an activation switch opening 170 for receiving the momentary activation switch 100, a microphone opening 180 for receiving the microphone 40, a microphone switch opening 190 for receiving the microphone switch 110 and an indicator opening 200 for receiving an indicator light 210. The power source 80, preferably a dry cell battery is located within the housing 70.

Figure 1:
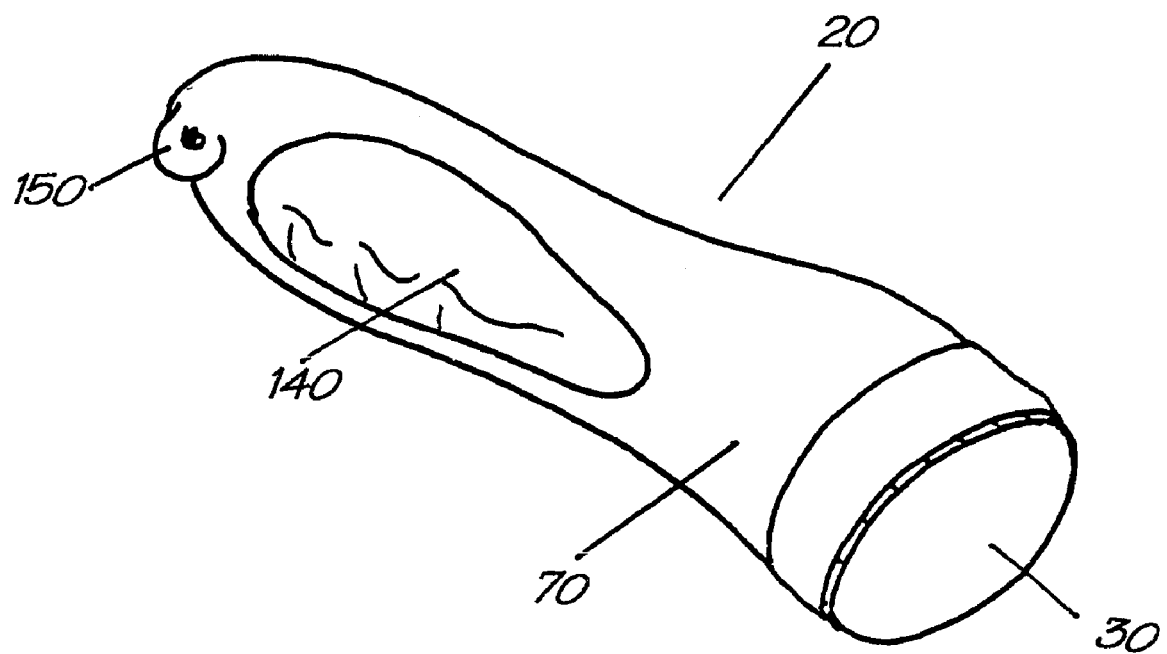
FIG. 1.
Figure 5:
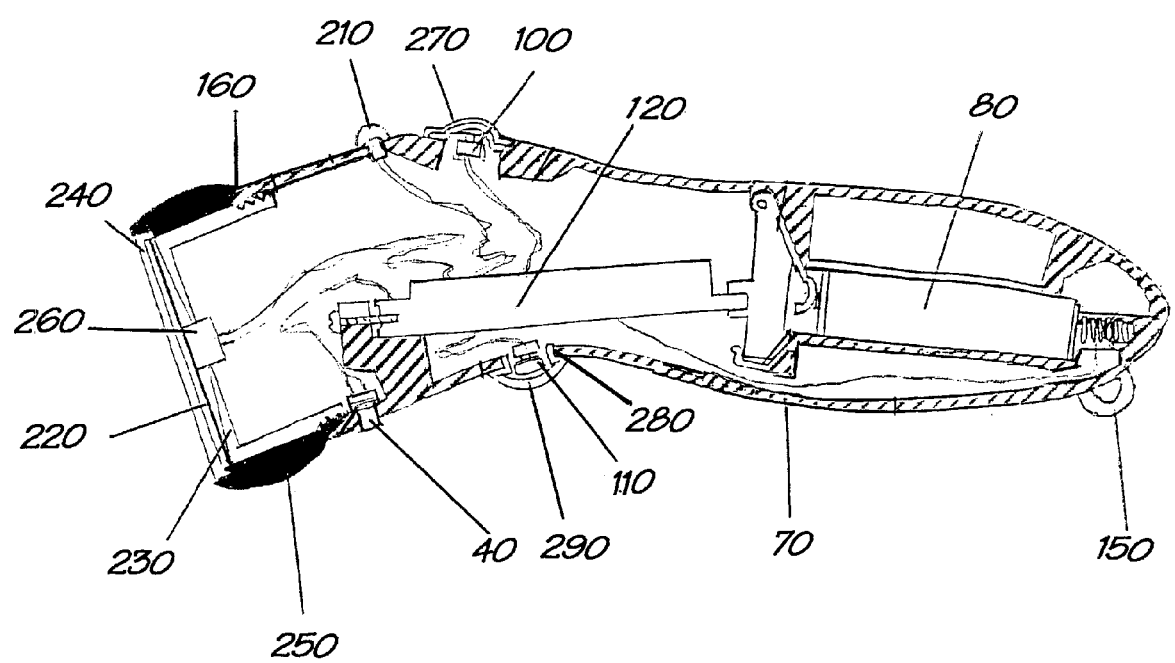
FIG. 5.

The stethoscope head 30 shown in FIGS. 1, 3 and 5 is located within the head opening 160 of the housing 70 and is connected in circuit to the power source 80 and the transmitter 120. The stethoscope head 30 comprises a diaphragm 220, a stethoscope bell 230, a first fluid tight cover 240, a fluid tight member 250 and a low frequency response microphone 260 for sensing auscultatory sounds created by patient internal biological functions. The fluid tight member 250 between the stethoscope head 30 and the head opening 160 maintains the fluid tight integrity of the housing 70 and provides shock resistance protection to the stethoscope head 30. The indicator light 210 indicates power flow to the stethoscope head 30 when the momentary activation switch 100 is actuated.

Figure 2:
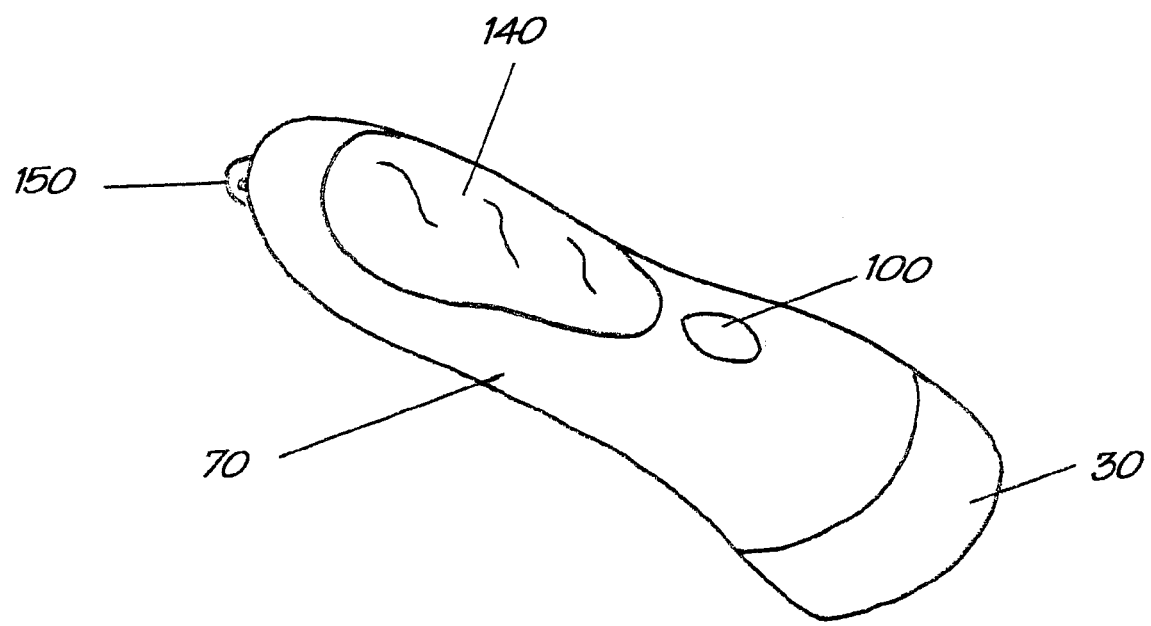
FIG. 2.
Figure 3:
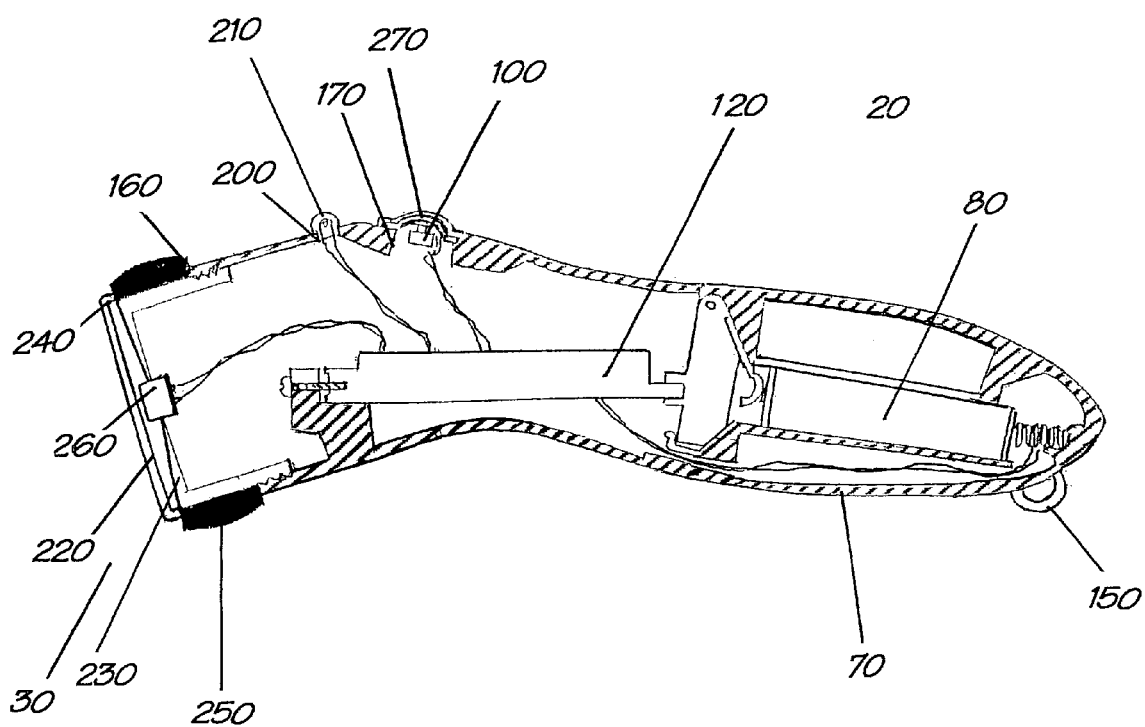
FIG. 3.

The momentary activation switch 100 shown in FIGS. 2, 3 and 5 is situated within the activation switch opening 170 and is connected in circuit to the stethoscope head 30. The low frequency response microphone 260 of the stethoscope head 30 is activated when the momentary activation switch 100 is actuated. A second fluid tight cover 270 is placed over the momentary activation 100 to seal the activation switch opening 170.

The microphone 40 is an optional feature of the sound sensing device 20 as shown in FIG. 5. The microphone 40 is used for sensing other communications that may not otherwise be heard by a person wearing a HAZMAT suit. A second fluid tight member 280 between the microphone 40 and the microphone opening 180 maintains the fluid tight integrity of the housing 70. The microphone activation switch 110 is connected in circuit to the microphone 40 for activating the microphone 40. A third fluid tight cover 290 over the microphone switch seals the microphone switch opening 190.

The transmitter 120 shown in FIGS. 3 and 5 is located within the fluid tight housing 70 and is connected in circuit to the power source 80 for transmitting the first signal and second signal to the receiver 50. The sound sensing device 20 may use several different types of transmitter to effectuate the intended purpose of the cordless stethoscope 10. Preferably, the sound sensing device 20 uses a magnetic induction transmitter to transmit the digital signals to the receiver 50 by way of an omni directional magnetic field. Magnetic induction is preferred over using radio wave transmission due to decreased interference and avoidance of compatibility issues with other medical equipment.

Figure 6:
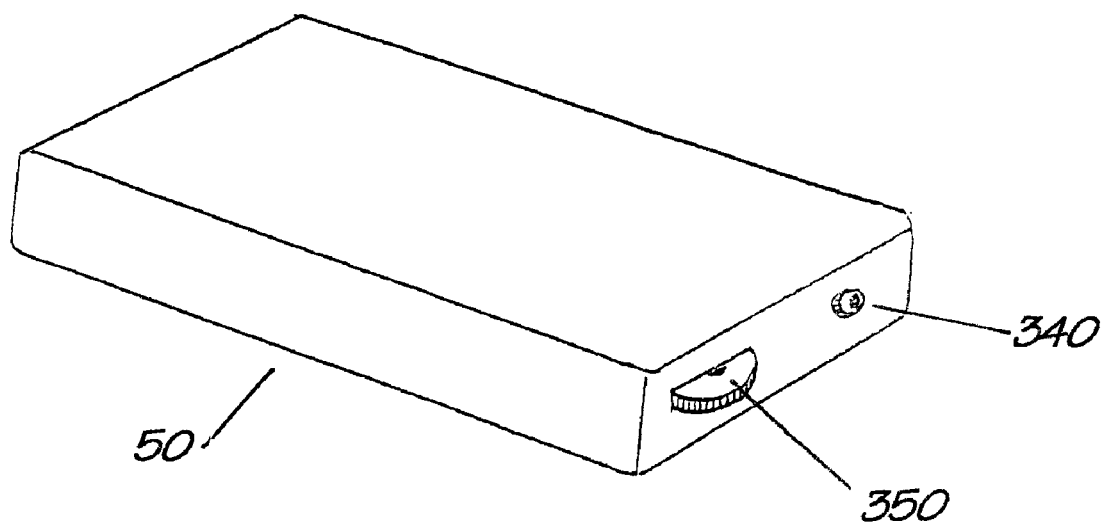
FIG. 6.
Figure 7:
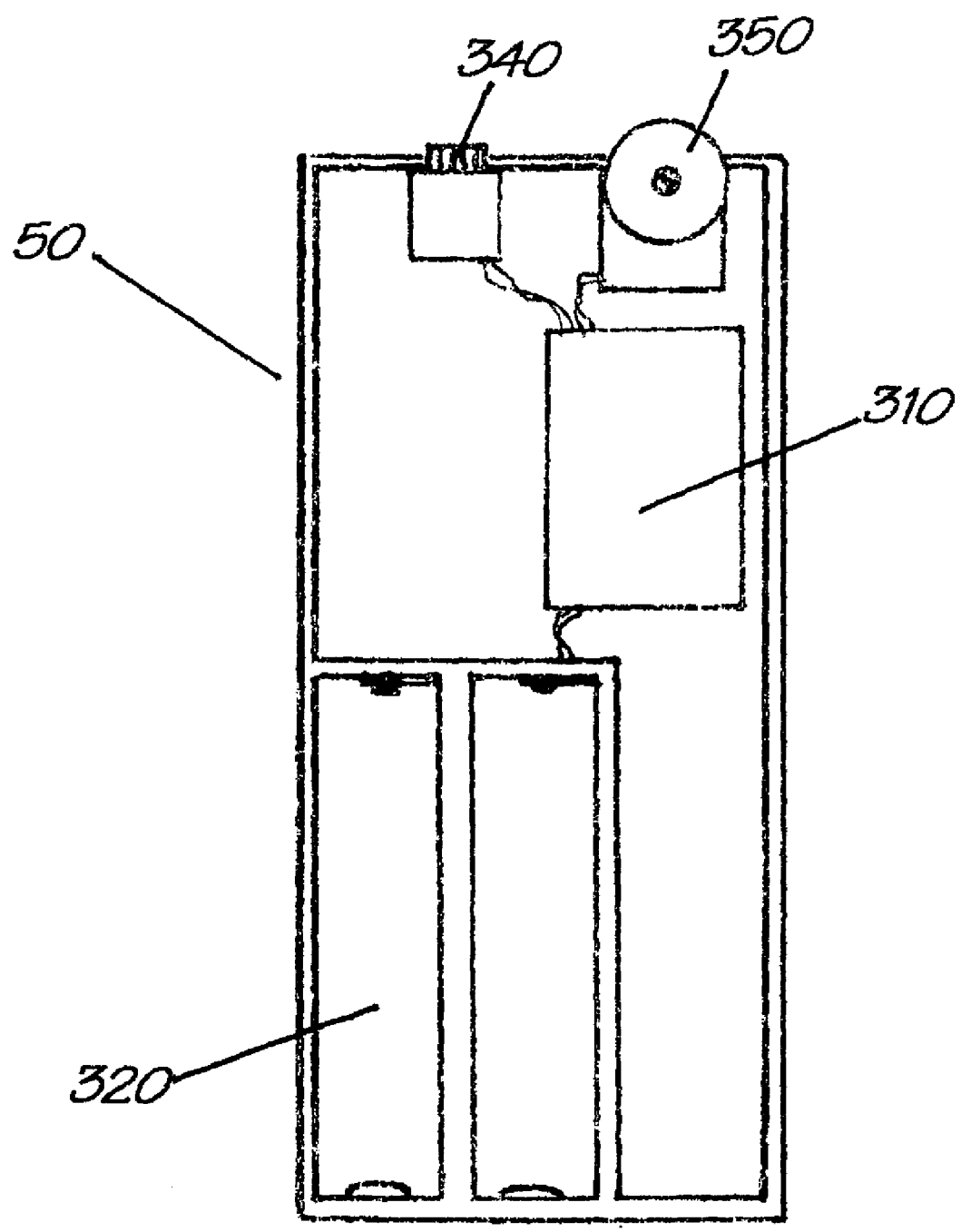
FIG. 7.

The receiver 50 shown in FIGS. 6–8 generally comprises a receiver housing 300, a receiver module 310, a receiver power source 320, an earpiece jack 340 and a receiver volume control 350. The receiver module 310 may use several different types of receiver to effectuate the intended purpose of the cordless stethoscope 10. Preferably, the receiver module 310 uses a magnetic induction receiver for receiving the magnetic field transmitted by the magnetic induction transmitter 120.

The earpieces 60 convert the magnetic field transmissions transmitted by the transmitter 120 and received by the receiver module 310 into first and second analog signal that are converted into audible sound for the person using the cordless stethoscope 10 to hear the auscultatory sound and sound communication gathered by the sound sensing device 20. The first and second analog signals may also be cordlessly transmitted from the receiver 50 to the earpieces 60.

Figure 4:
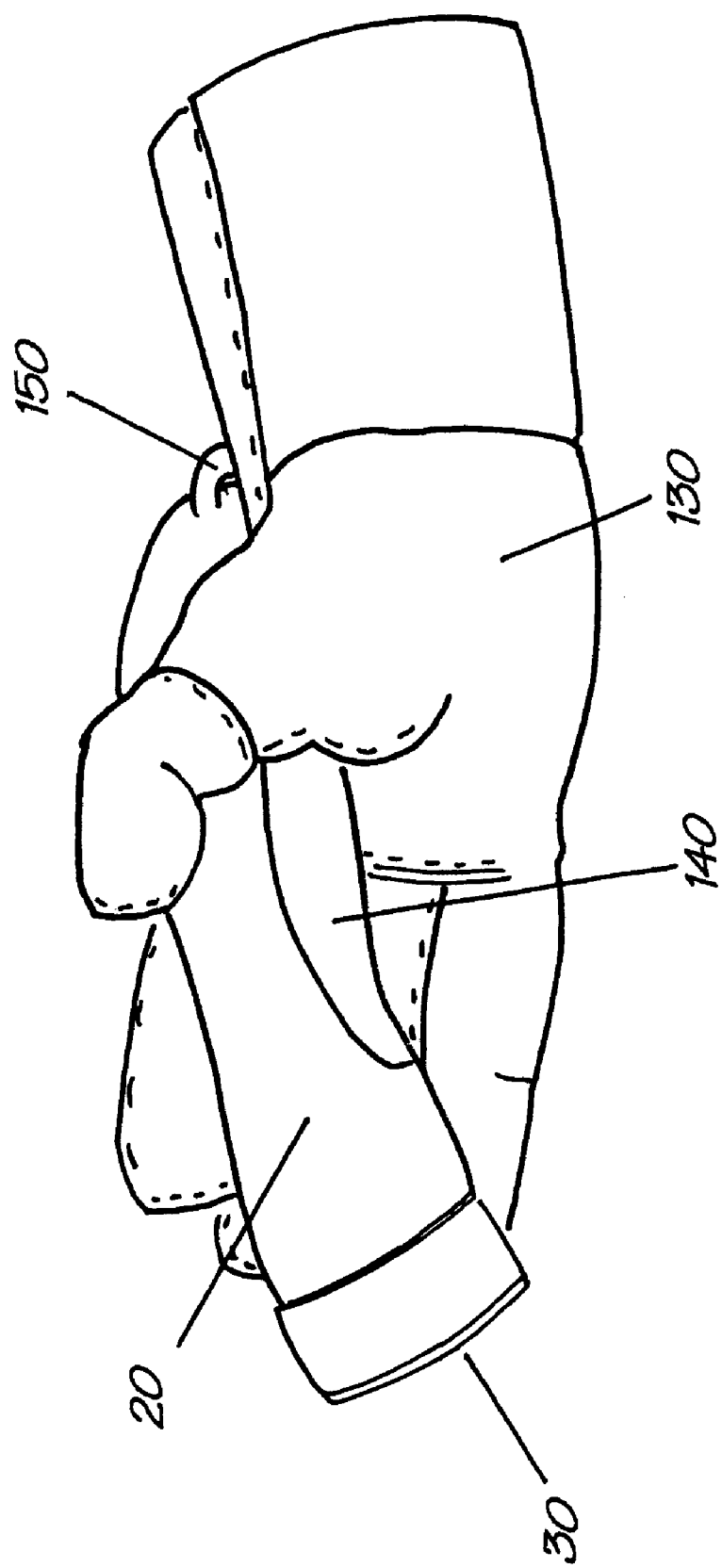
FIG. 4.

The cordless stethoscope for hazardous material environments 10 may be sold in a kit type form as shown in FIG. 8 and is used by placing the earpieces 60 within the ears of the user and the receiver 50 within a pocket or clipped onto a belt within the HAZMAT suit worn by the user. The sound sensing device 20 is then used as shown in FIG. 4 by placing the activated device 20 adjacent a patient's body to gather auscultatory information that is transmitted via the transmitter 120 to the receiver module 310 where the signal is converted into audible sound by the earpiece for assessment by the user of the cordless stethoscope 10.

While the above description contains much specificity, this specificity should not be construed as limitations on the scope of the invention, but rather as an exemplification of the invention. For example, it is contemplated that the spirit of the present invention essentially discloses a stethoscope comprising no external cords or wires. Hence, the stethoscope of the present invention is cordless. The cordless stethoscope of the present invention is designed for use in hazardous material environments such as those hereinabove specified, and in this regard, comprises a fluid-impermeable or fluid tight, hand-holdable casing assembly (such as fluid tight housing 70), a cordless data transmitter (such as transmitter 120), a remote receiver (such as receiver 50), and a sound reproduction device (such as ear piece or ear pieces 60).

It will be understood that the casing assembly is preferably sized and shaped to being grasped by a (gloved) human hand and manually operated with the human hand. The casing assembly essentially comprises a stethoscope head end (such as stethoscope head 30), which functions to receive auscultatory sound data or sound wave energy as inherently described hereinabove. Notably, the data transmitter is housed within the casing assembly for transmitting the auscultatory sound data received by the stethoscope head end to the remote receiver (without the aid of external wires or cords). The remote receiver then relays the auscultatory sound data transmissions as received from the data transmitter to the sound reproduction device, which sound reproduction device converts the relayed auscultatory sound data transmissions into audible sounds for diagnosis and/or treatment by users outfitted with or adjacent the sound reproduction device.

The cordless stethoscope may additionally comprise a microphone assembly (such as microphone 40), which assembly is preferably in electrical communication with the data transmitter for relaying voice sound data or sound wave energy to the data transmitter. In this regard, the data transmitter may also function to transmit voice sound data as received by the microphone assembly to the remote receiver. The remote receiver, in turn, functions to relay the voice sound data transmissions from the data transmitter to the sound reproduction device for converting the relayed voice sound data transmissions into audible sounds.

Preferably, the data transmitter of the disclosed cordless stethoscope is a magnetic induction type transmitter, which relays the auscultatory sound data to the remote receiver via an omni directional magnetic field. It will be recalled that magnetic induction type transmission for this type of device is to be preferred over using radio wave electromagnetic type transmission due to decreased interference and avoidance of compatibility issues with other peripheral medical equipment. It will thus be understood that the magnetic induction type transmitter functions to enhance cooperative usage of the cordless stethoscope along side or in cooperative association with peripheral (medical) equipment, which often operate utilizing (otherwise interfering) radio wave-based electromagnetic energy.

Accordingly, although the invention has been described by reference to a number of preferred embodiments, it is not intended that the novel device as taught by the foregoing descriptions be limited thereby, but that modifications thereof are intended to be included as falling within the broad scope and spirit of the foregoing disclosure, the following claims and the appended drawings.

I claim:

1. A cordless stethoscope system for use in hazardous material environments, the cordless stethoscope system comprising:
   a housing, the housing being graspable by a gloved hand and comprising a fluid tight portion, a head opening, an activation switch opening, a microphone opening and a microphone switch opening;
   a power source, the power source being housed within the fluid tight portion;
   a stethoscope head, the stethoscope head being positioned within the head opening of the housing for sensing auscultatory sounds and having a first fluid tight member, the first fluid tight member being positioned between the stethoscope head and the head opening and connected in circuit to the power source;
   a fluid tight cover, the fluid tight cover being positioned over the stethoscope head for sealing the head opening;
   a momentary activation switch, the momentary activation switch being positioned within the activation switch opening and connected in circuit to the stethoscope head for activating the stethoscope head when the momentary activation switch is actuated;
   a second fluid tight cover, the second fluid tight cover being positioned over the momentary activation switch for sealing the activation switch opening;
   a microphone, the microphone being positioned within the microphone opening for sensing sound communications and having a second fluid tight member, the second fluid tight member being positioned between the microphone and the microphone opening and connected in circuit to the power source;
   a microphone activation switch, the microphone activation switch being positioned within the microphone switch opening and connected in circuit to the microphone for activating the microphone when the microphone activation switch is actuated;
   a third fluid tight cover, the third fluid tight cover being positioned over the microphone switch for sealing the microphone switch opening;
   a magnetic induction transmitter, the magnetic induction transmitter being housed within the fluid tight portion and connected in circuit to the power source for transmitting the auscultatory sound sensed by the stethoscope head and sound communications sensed by the microphone in a magnetic field;
   a receiver housing;
   a receiver power source, the receiver power source being positioned within the receiver housing;
   a magnetic induction receiver, the magnetic induction receiver being housed within the receiver housing and connected in circuit to the receiver power source for receiving the magnetic field containing the auscultatory sound and sound communications; and
   an ear piece, the ear piece being connected in circuit to the magnetic induction receiver for converting the magnetic field received by the receiver into audible sound.

2. The cordless stethoscope system of claim 1 wherein the housing further comprises an indicator opening and an indicator for indicating power flow to the stethoscope head, the indicator being positioned within the indicator opening and connected in circuit to the power source.

3. The cordless stethoscope system of claim 2 wherein the housing further comprises a ring, the ring providing means for attaching the housing to another object.

4. The cordless stethoscope system of claim 1 further comprising a no slip grip connected to an outer portion of the housing, the no slip grip thus for enhancing a user's ability to grasp the housing.

5. A sound sensing device for use in hazardous material environments, the device comprising:
- a housing, the housing being graspable by a gloved hand and comprising a fluid tight portion, a head opening, an activation switch opening, a microphone opening and a microphone switch opening;
- a power source, the power source being housed within the fluid tight portion;
- a stethoscope head, the stethoscope head being positioned within the head opening of the housing for sensing auscultatory sounds and having a first fluid tight member, the first fluid tight member being positioned between the stethoscope head and the head opening and connected in circuit to the power source;
- a momentary activation switch, the momentary activation switch being positioned within the activation switch opening and connected in circuit to the stethoscope head for activating the stethoscope head when the momentary activation switch is actuated;
- a first fluid tight cover, the first fluid tight cover being positioned over the momentary activation switch for sealing the activation switch opening;
- a microphone, the microphone being positioned within the microphone opening for sensing sound communications and having a second fluid tight member, the second fluid tight member being positioned between the microphone and the microphone opening and connected in circuit to the power source;
- a microphone activation switch, the microphone activation switch being positioned within the microphone switch opening and connected in circuit to the microphone for activating the microphone when the microphone activation switch is actuated;
- a second fluid tight cover, the second fluid tight cover being positioned over the microphone switch for sealing the microphone switch opening; and
- a magnetic induction transmitter, the magnetic induction transmitter being housed within the fluid tight portion and connected in circuit to the power source for transmitting the auscultatory sound sensed by the stethoscope head and the sound communications sensed by the microphone.

6. The device of claim 5 wherein the housing further comprises an indicator opening and an indicator for indicating power flow to the stethoscope head, the indicator being positioned within the indicator opening and connected in circuit to the power source.

7. The device of claim 6 wherein the housing further comprises a ring, the ring providing means for attaching the housing to another object.

8. The device of claim 5 further comprising a no slip grip connected to an outer portion of the housing, the no slip grip for enhancing a user's ability to grasp the housing.

* * * * *